(12) United States Patent
Zamyatin et al.

(10) Patent No.: US 9,724,056 B2
(45) Date of Patent: *Aug. 8, 2017

(54) METHOD AND SYSTEM FOR SPECTRAL COMPUTED TOMOGRAPHY (CT) WITH INNER RING GEOMETRY

(71) Applicant: TOSHIBA MEDICAL SYSTEMS CORPORATION, Otawara-Shi, Tochigi-Ken (JP)

(72) Inventors: Alexander Zamyatin, Hawthorn Woods, IL (US); Yu Zou, Naperville, IL (US); Xiaolan Wang, Buffalo Grove, IL (US); Zhengyan Wang, Antioch, IL (US); Yuexing Zhang, Naperville, IL (US)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 704 days.

This patent is subject to a terminal disclaimer.

(21) Appl. No.: 14/092,998

(22) Filed: Nov. 28, 2013

(65) Prior Publication Data

US 2015/0146844 A1    May 28, 2015

(51) Int. Cl.
*A61B 6/03* (2006.01)
*A61B 6/00* (2006.01)
*G01T 1/24* (2006.01)

(52) U.S. Cl.
CPC ............ *A61B 6/4241* (2013.01); *A61B 6/032* (2013.01); *A61B 6/4007* (2013.01); *A61B 6/4275* (2013.01); *A61B 6/482* (2013.01); *G01T 1/243* (2013.01)

(58) Field of Classification Search
CPC  G01T 1/24; G01T 1/243; A61B 6/032; A61B 6/482; A61B 6/4241; A61B 6/4014; A61B 6/4266; A61B 6/4208; A61B 6/4007; A61B 6/4275
USPC ............................................................. 378/5
See application file for complete search history.

(56) References Cited

U.S. PATENT DOCUMENTS

| | | | | |
|---|---|---|---|---|
| 5,379,333 A * | 1/1995 | Toth | ........................ | A61B 6/032 378/108 |
| 6,256,369 B1 * | 7/2001 | Lai | ......................... | A61B 6/032 378/14 |
| 7,646,845 B2 * | 1/2010 | Lecomte | ................ | A61B 6/032 378/19 |
| 9,285,326 B2 * | 3/2016 | Gagnon | .................. | A61B 6/032 |
| 2005/0226364 A1 * | 10/2005 | Bernard De Man | .. | A61B 6/032 378/9 |
| 2007/0147574 A1 * | 6/2007 | Bernard De Man | .. | A61B 6/032 378/4 |
| 2007/0205367 A1 * | 9/2007 | Deman | .................. | G01T 1/2985 250/363.02 |
| 2007/0206721 A1 * | 9/2007 | Tkaczyk | ................ | A61B 6/032 378/19 |

(Continued)

*Primary Examiner* — Wyatt Stoffa
(74) *Attorney, Agent, or Firm* — Kenichiro Yoshida

(57) ABSTRACT

Photon counting detectors are sparsely placed at predetermined positions in the fourth-generation geometry around an object to be scanned in spectral Computer Tomography (CT). An X-ray emitting source rotates radially outside the sparsely placed photon counting detectors. Furthermore, the integrating detectors are placed in the third-generation in combination to the sparsely placed photon counting detectors at predetermined positions in the fourth-generation geometry.

34 Claims, 10 Drawing Sheets

(56) References Cited

U.S. PATENT DOCUMENTS

| | | | | |
|---|---|---|---|---|
| 2008/0118024 A1* | 5/2008 | Cho | A61B 6/00 378/13 |
| 2008/0277591 A1* | 11/2008 | Shahar | A61B 6/032 250/394 |
| 2009/0161816 A1* | 6/2009 | De Man | A61B 6/032 378/9 |
| 2010/0215142 A1* | 8/2010 | Dafni | A61B 6/032 378/19 |
| 2010/0246754 A1* | 9/2010 | Morton | A61B 6/032 378/9 |
| 2011/0026685 A1* | 2/2011 | Zilberstein | G01T 1/1611 378/197 |
| 2012/0087481 A1* | 4/2012 | Litvin | A61B 6/032 378/207 |
| 2012/0093281 A1* | 4/2012 | Zamyatin | A61B 6/032 378/15 |
| 2012/0104262 A1* | 5/2012 | Wiegert | G01N 23/046 250/363.03 |
| 2012/0213424 A1* | 8/2012 | Flohr | A61B 6/4014 382/131 |
| 2013/0004050 A1* | 1/2013 | Wu | A61B 6/032 382/132 |
| 2013/0058450 A1* | 3/2013 | Liu | A61B 6/032 378/7 |
| 2013/0251097 A1* | 9/2013 | Zou | A61B 6/032 378/9 |
| 2014/0056407 A1* | 2/2014 | Goldammer | A61B 6/5205 378/62 |
| 2014/0241489 A1* | 8/2014 | Zhang | A61B 6/5282 378/7 |
| 2014/0328452 A1* | 11/2014 | Tsubota | A61B 6/032 378/7 |
| 2015/0131775 A1* | 5/2015 | Yorkston | A61B 6/4405 378/17 |
| 2015/0230766 A1* | 8/2015 | Wang | A61B 6/4417 600/411 |
| 2015/0359496 A1* | 12/2015 | Tsukerman | A61B 6/5205 600/436 |
| 2015/0366527 A1* | 12/2015 | Yu | A61B 5/055 382/131 |
| 2016/0128650 A1* | 5/2016 | Wang | A61B 6/482 378/5 |

* cited by examiner

METHOD AND SYSTEM FOR SPECTRAL COMPUTED TOMOGRAPHY (CT) WITH INNER RING GEOMETRY

One related patent application, Ser. No. 13/426,903 has been filed on Mar. 22, 2012 for disclosing a combination of conventional energy integrating detectors and photon counting detectors.

FIELD OF THE INVENTION

The current invention is generally related to an image processing and system, and more particularly related to sparse photon counting detectors with an inner ring geometry for spectral Computer Tomography (CT).

BACKGROUND OF THE INVENTION

The x-ray beam in most computer tomography (CT) scanners is generally polychromatic. Yet, most of the currently used CT scanners generate images based upon data according to the energy integration nature of the detectors. These conventional detectors are called energy integrating detectors for acquiring energy integration X-ray data. On the other hand, photon counting detectors are configured to acquire the spectral nature of the x-ray source rather than the energy integration nature in acquiring data. To obtain the spectral nature of the transmitted X-ray data, the photo counting detectors split the x-ray beam into its component energies or spectrum bins and counts a number of photons in each of the bins. The use of the spectral nature of the x-ray source in CT is often referred to as spectral CT. Since spectral CT involves the detection of transmitted X-ray at two or more energy levels, spectral CT generally includes dual-energy CT by definition.

Spectral CT is advantageous over conventional CT. Spectral CT offers the additional clinical information inherent in the full spectrum of an x-ray beam. For example, spectral CT facilitates in discriminating tissues, differentiating between materials such as tissues containing calcium and iodine or enhancing the detection of smaller vessels. Among other advantages, spectral CT is also expected to reduce beam hardening artifacts. Spectral CT is also expected to increase accuracy in CT numbers independent of scanners.

All of these prior art attempts for spectral CT involve tradeoffs while trying to solve issues such as beam hardening, temporal resolution, noise balance, and inadequate energy separation. For example, dual source solutions are good for noise balance and energy separation but are not so good in some clinical applications for correcting beam hardening and improving temporal resolution. Fast kV-switching has the potential for good beam hardening correction and good temporal resolution although the noise balance might require a tradeoff with temporal resolution and inadequate energy separation might affect the precision of the reconstructed spectral images. Nonetheless, when used in the right clinical situations, prior art solutions can be used successfully to improve diagnosis. On the other hand, doing spectral imaging with photon counting detectors has the potential for solving all four issues without tradeoffs as well as more advanced spectral techniques such as precise material characterization through k-edge imaging.

Prior art has also attempted to replace the conventional integrating detectors by the photon counting detectors in implementing spectral CT. In general, photon counting detectors are costly and have performance constraints under high flux x-rays. Although at least one experimental spectral CT system has been reported, the costs of high-rate photon counting detectors are prohibitive for a full-scale implementation. Despite some advancement in the photon counting detector technology, the currently available photon counting detectors still require solutions to implementation issues such as polarization due to space charge build-up, pile-up effects, scatter effects, spatial resolution, temporal resolution and dose efficiency.

For the above reasons, it is still desired to invent spectral CT systems for improving the use of the photon counting detectors in view of the above issues.

DETAILED DESCRIPTION OF THE EMBODIMENT(S)

Figure 1:
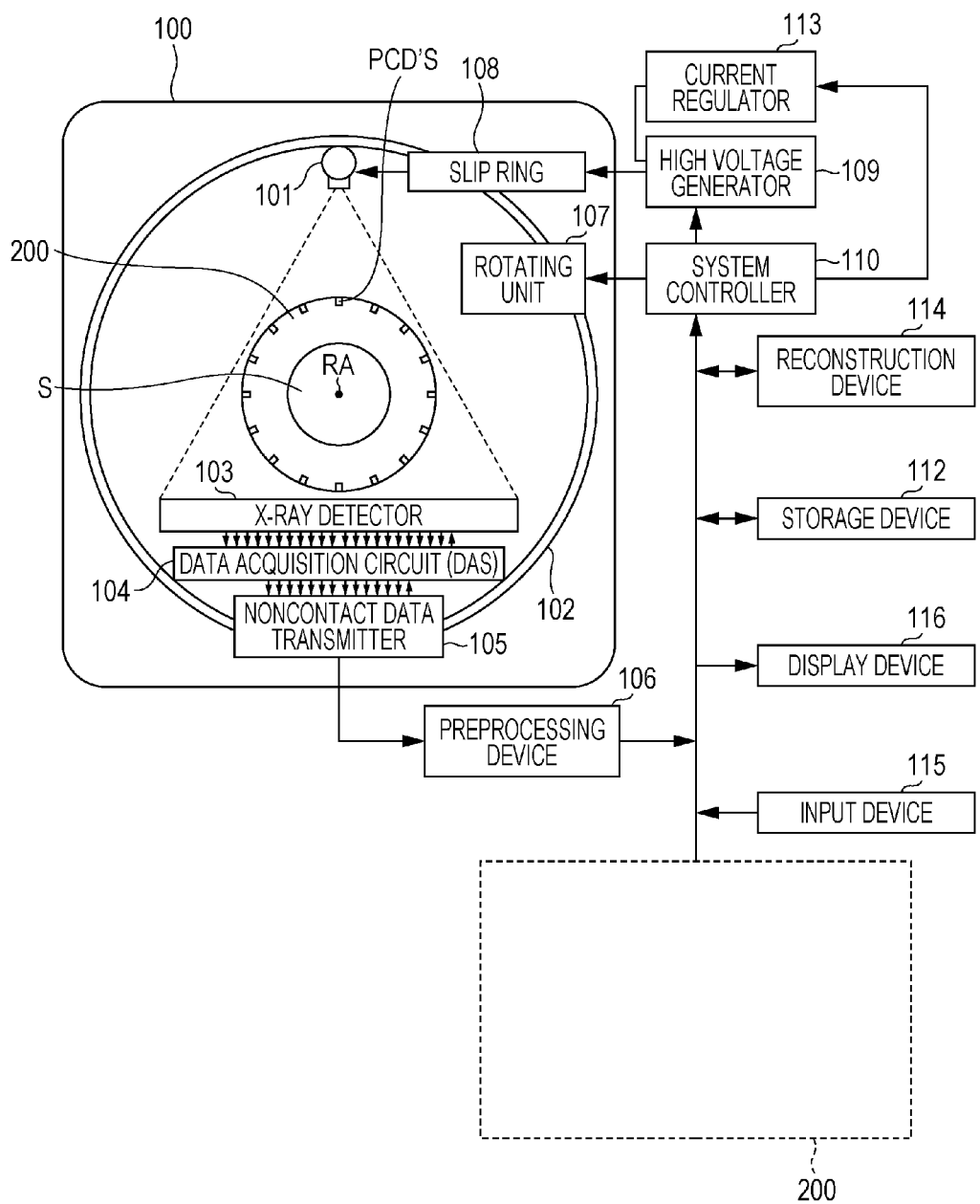
FIG. 1 is a diagram illustrating one X-ray CT apparatus or scanner according to the current invention including a gantry and other devices or units.

Referring now to the drawings, wherein like reference numerals designate corresponding structures throughout the views, and referring in particular to FIG. 1, a diagram illustrates one X-ray CT apparatus or scanner according to the current invention including a gantry 100 and other devices or units. The gantry 100 is illustrated from a side view and further includes an X-ray tube 101, an annular frame 102 and a multi-row or two-dimensional array type X-ray detector 103. The X-ray tube 101 and X-ray detector 103 are diametrically mounted across a subject S on the annular frame 102, which is rotatably supported around a rotation axis RA. A rotating unit 107 rotates the frame 102 at a high speed such as 0.4 sec/rotation while the subject S is being moved along the axis RA into or out of the illustrated page.

The multi-slice X-ray CT apparatus further includes a high voltage generator 109 that generates a tube voltage to be applied to the X-ray tube 101 through a slip ring 108 so that the X-ray tube 101 generates X ray. The X rays are emitted towards the subject S, whose cross sectional area is represented by a circle. The X-ray detector 103 is located at an opposite side from the X-ray tube 101 across the subject S for detecting the emitted X rays that have transmitted through the subject S. The X-ray detector 103 further includes individual detector elements or units that are conventional integrating detectors.

Still referring to FIG. 1, the X-ray CT apparatus or scanner further includes other devices for processing the detected signals from X-ray detector 103. A data acquisition circuit or a Data Acquisition System (DAS) 104 converts a signal output from the X-ray detector 103 for each channel into a voltage signal, amplifies it, and further converts it into a digital signal. The X-ray detector 103 and the DAS 104 are configured to handle a predetermined total number of projections per rotation (TPPR) that can be at the most 900 TPPR, between 900 TPPR and 1800 TPPR and between 900 TPPR and 3600 TPPR.

The above described data is sent to a preprocessing device 106, which is housed in a console outside the gantry 100 through a non-contact data transmitter 105. The preprocessing device 106 performs certain corrections such as sensitivity correction on the raw data. A storage device 112 then stores the resultant data that is also called projection data at a stage immediately before reconstruction processing. The storage device 112 is connected to a system controller 110 through a data/control bus, together with a reconstruction device 114, input device 115, display device 116 and the scan plan support apparatus 200. The scan plan support apparatus 200 includes a function for supporting an imaging technician to develop a scan plan.

The detectors are either rotated or fixed with respect to the patient among various generations of the CT scanner systems. The above described CT system has one exemplary third-generation geometry in which the X-ray tube 101 and the energy integrating X-ray detector 103 are diametrically mounted on the annular frame 102 and are moved around the subject S as the annular frame 102 is rotated about the rotation axis RA. On the other hand, a fourth-generation geometry has energy differentiating detectors that are fixedly placed around the patient S.

In one embodiment according to the current invention, a predetermined number of energy differentiating detectors such as photon counting detectors PCD and semiconductor direct conversion detectors are fixedly placed along an object along a predetermined path 200. As illustrated in FIG. 1, the photon counting detectors PCD are sparsely mounted inside or along the predetermined path 200, which is located between a first trajectory of the energy integrating detector 103 and a second trajectory of the radiation emitting source or X-ray tube 101. In the illustrated embodiment, the trajectory of the source tube 101 is illustrated to have the largest diameter so that a predetermined beam angle encompasses substantially all of the portions of the predetermined path 200. In another embodiment, the trajectory of the source tube 101 may have a certain diameter that a predetermined beam angle may not encompass all of the portions of the predetermined path 200.

In the above described relative spatial relationship, the radiation emitting source 101 is moved along the predetermined path outside the first path of the fixedly placed photon counting detectors PCD while continuously emitting radiation towards the object. In this regard, the X-ray that is emitted from the source 101 towards the subject S, and some radiation reaches the energy integrating detector 103 after transmitted through the subject S while other radiation also reaches a certain portion of the energy differentiating detectors PCD, whose detection surface is located at a certain angle with respect to the source 101. Spectral data is detected at the energy differentiating detectors PCD, which are sparsely fixed with respect to the source 101. Energy integration data is detected at the energy integrating detector 103, which is rotated with the source 101. Thus, both the energy integrating detector 103 and the energy differentiating detectors PCD continuously acquire a combination of the data for later reconstructing an image at the reconstruction device 114. In any case, FIG. 1 illustrates a combined use of the rotating energy integrating detector 103 and the fixedly mounted energy differentiating detectors PCD in the above described certain relative spatial relationship.

As will be further illustrated, the above described embodiment is a mere example and is not limited in many aspects. For example, although a certain spatial relationship of the trajectories or paths are disclosed among the source 101, the energy differentiating detectors PCD and the energy integrating detector 103, the spatial relationship is relative and not limited to a particular relation as illustrated in the diagram. Another example is that the energy differentiating detectors PCD are mounted inside the gantry 100 in the illustrated embodiment while the energy differentiating detectors PCD of another embodiment are initially mounted in a retrofitting unit or device that is not illustrated in FIG. 1 before the retrofitting device is placed in an existing CT scanner system. Lastly, although a single pair of the energy integrating detector 103 and the radiation source 101 is illustrated in the embodiment, an additional pair of the energy integrating detector 103 and the radiation source 101 is incorporated in another embodiment according to the current invention.

Figure 2:
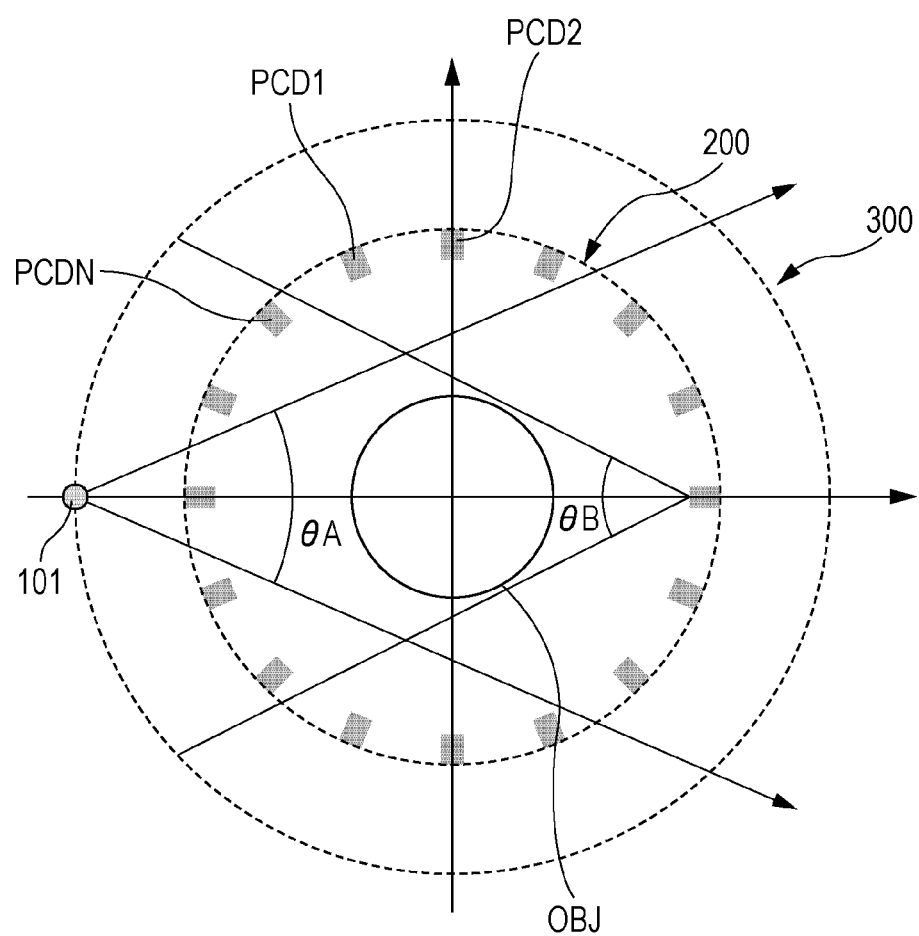
FIG. 2 is a diagram illustrating one embodiment for placing the photon counting detectors (PCD) in a predetermined fourth-generation geometry in the CT scanner system according to the current invention.

Now referring to FIG. 2, a diagram illustrates one embodiment for placing the photon counting detectors (PCD) in a predetermined fourth-generation geometry in the CT scanner system according to the current invention. The diagram merely illustrates a relative relationship among an object or a patient OBJ to be scanned, an X-ray source or radiation emitting source 101 and photon counting detectors PCD1 through PCDN in one exemplary embodiment. For the sake of simplicity, the diagram excludes other components and units that may be necessary in acquiring and processing data as well as reconstructing an image based upon the acquired data. In general, the photon counting detectors PCD1 through PCDN are made of a device and output a photon count for each of predetermined energy components. Although approximately one hundred to three hundred photon counting detectors are utilized in certain embodiments, the above numerical range of the photon counting detectors is merely exemplary, and the claimed invention is not necessarily limited to any particular number of the photon counting detectors.

Still referring to FIG. 2, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. On the other hand, the X-ray source 101 is located outside the circular component 200 and is mounted on a rotating portion 300 such as the annular frame 102 in the gantry 100 so that the X-ray source 101 projects X-ray with a predetermined source fan beam angle θ A towards the object OBJ while the X-ray source 101 rotates around the object OBJ outside the sparsely placed photon counting detectors PCD1 through PCDN. Consequently, the photon counting detectors PCD1 through PCDN individually detect with a predetermined detector fan beam angle θ B the X-ray that has been transmitted through the object OBJ and output a number of photons for each of predetermined energy components.

In certain embodiments, the energy differentiating detectors PCD1 through PCDN are initially housed in the module housing of a modular retrofitting unit or device 200 as illustrated in FIG. 2 before the retrofitting device is placed in an existing CT scanner system. The above described modular retrofitting device is optionally used with other embodiments such as illustrated in FIGS. 3 through 5 and 11. That is, the modular device 200 with the energy differentiating detectors is retrofitted in an existing image scanner for reconstructing an image. The image scanner rotates a radiation emitting source along a first path around a predetermined center while continuously emits energy towards an object. The image scanner optionally rotates an energy integrating detector for detecting intensity data along a second path around the predetermined center. The modular device further includes a predetermined number of energy differentiating detectors for detecting spectral data and a module housing for housing a predetermined number of the energy differentiating detectors that are fixedly placed along a third path, third path being inside the first path as the module housing is retrofitted into the existing image scanner, whereas the scanner reconstructs an image based upon the intensity data and the spectral data. The above described paths include certain predetermined trajectories such as a circumference, a helix and a polygon, but are not limited to a particular set of predetermined paths in a predetermined combination. Furthermore, the size of the modular retrofitting unit or device 200 is not necessarily limited to a gantry or a housing of the existing CT scanner system. The modular retrofitting unit or device 200 is also optionally attached to a gantry or a housing of the existing CT scanner system in a detachable or fixed manner.

FIG. 2 also discloses that the X-ray from the source 101 travels through openings or gaps between the sparsely placed photon counting detectors PCD1 through PCDN towards the object OBJ. Some portion of the emitted X-ray is blocked by certain ones of the sparsely placed photon counting detectors PCD1 through PCDN depending upon an angle with respect to the source 101. In other words, a certain portion of the emitted X-ray projects onto the back surface of some of the sparsely placed photon counting detectors PCD1 through PCDN at any given time as the source 101 is rotated around the predetermined trajectory 300. The remaining X-ray travels through the gap and reaches certain ones of the photon counting detectors PCD1 through PCDN, whose detecting surface is facing the source 101 and is substantially within the predetermined source fan beam angle θ A, and each of these photon counting detectors PCD1 through PCDN individually detect with the predetermined detector fan beam angle θ B.

In the above embodiment, the photon counting detectors (PCD) are sparsely and fixedly placed along a first circular path around the object OBJ while at least one X-ray source 101 rotates along a second circular path around the object OBJ. Furthermore, the above embodiment illustrates that the first circular path is smaller and inside the second circular path around the object OBJ. There are other alternative embodiments for placing the photon counting detectors (PCD) in a predetermined fourth-generation geometry in the CT scanner system according to the current invention. Although it is not illustrated in a drawing, an alternative embodiment optionally includes a first path that is substantially circular and also a non-circular first path such as a predetermined polygon along which the photon counting detectors PCD1 through PCDN are sparsely placed.

Again, although it is not illustrated in a drawing, an alternative embodiment optionally includes more than one X-ray source 101, and a plurality of the X-ray sources 101 is mounted on the rotating portion 300 such as the annular frame 102 at a predetermined angle with each other. At least one of the X-ray sources 101 is optionally a single energy source in certain embodiments. By the same token, a second alternative embodiment optionally includes the X-ray source 101, which is configured to perform a kV-switching function for emitting X-ray at a predetermined high-level energy and a predetermined low-level energy. Furthermore, the radiation emitting source or the X-ray source 101 optionally modulates a combination of a radiation energy level and an intensity level over time.

The above embodiment according to the current invention also provides a protective rear cover for each of the photon counting detectors PCD1 through PCDN that are irradiated from behind in a short distance. As the X-ray source 101 travels outside the first circular path of the sparsely placed photon counting detectors PCD1 through PCDN, the photon counting detectors PCD1 through PCDN are protected by the protective layer from the X-ray irradiation on the rear surface in order to substantially reduce undesirable effects as will be described with respect to FIG. 6.

Figure 3:
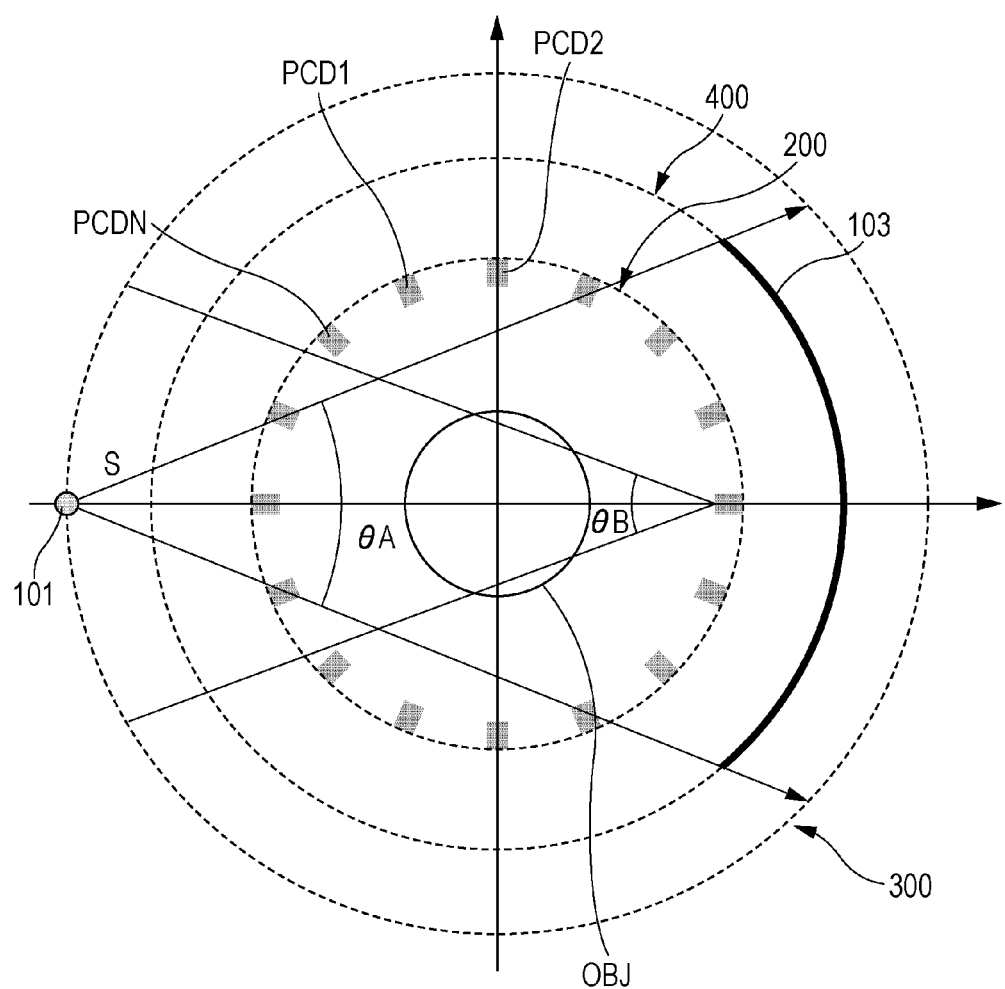
FIG. 3 is a diagram illustrating another embodiment for placing the photon counting detectors (PCD) in a predetermined fourth-generation geometry in combination with a detector unit in a predetermined third-generation geometry in the CT scanner system according to the current invention.

Now referring to FIG. 3, a diagram illustrates another embodiment for placing the photon counting detectors (PCD) in a predetermined fourth-generation geometry in combination with a detector unit in a predetermined third-generation geometry in the CT scanner system according to the current invention. The diagram merely illustrates a relative relationship among an object OBJ to be scanned, an X-ray source or radiation emitting source 101, an energy integrating detector 103 and the energy differentiating detectors PCD1 through PCDN in one exemplary embodiment. For the sake of simplicity, the diagram excludes other components and units that may be necessary in acquiring and processing data as well as reconstructing an image based upon the acquired data.

The embodiment utilizes a combination of the two types of detectors. In general, the photon counting detectors PCD1 through PCDN are made from a device and output a photon count for each of predetermined energy components. Although approximately one hundred to three hundred photon counting detectors are utilized in certain embodiments, the above numerical range of the photon counting detectors is merely exemplary, and the claimed invention is not necessarily limited to any particular number of the photon counting detectors. In addition to the sparsely placed photon counting detectors PCD1 through PCDN in the fourth-generation geometry, the embodiment of FIG. 3 now further includes an additional detector unit such as the energy integrating detector 103 in a third-generation geometry in the CT scanner system according to the current invention. The detector elements in the detector unit 103 are generally more densely placed along the detector unit surface than the photon counting detectors (PCD) in the exemplary embodiment. The detector surface of the detector unit 103 is optionally flexible, cylinder centered at iso-center at the source, sphere centered at the source or a flat panel.

Still referring to FIG. 3, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. The circular component 200 also provides a gap between the two adjacent ones of the photon counting detectors PCD1 through PCDN, and these gaps allows the transmission of the X-ray without substantial interference. Although it is not illustrated in a drawing, an alternative embodiment optionally includes a predetermined component 200 that is substantially circular and non-circular such as polygonal along which the photon counting detectors PCD1 through PCDN are sparsely placed.

Both the X-ray source 101 and the detector unit 103 rotate around the object OBJ while the photon counting detectors PCD1 through PCDN remain stationary with respect to the object OBJ. In one exemplary embodiment, the X-ray source 101 is mounted on a first rotating portion 300 such as the annular frame 102 in the gantry 100 so that the X-ray source 101 projects X-ray with a predetermined source fan beam angle θA towards the object OBJ while the X-ray source 101 rotates around the object OBJ outside the sparsely placed photon counting detectors PCD1 through PCDN. Furthermore, an additional detector unit 103 is mounted on a second rotating portion 400 in the third-generation geometry in the above exemplary embodiment of the CT scanner system according to the current invention. The rotating portion 400 mounts the detector unit 103 at a diametrically opposed position from the X-ray source 101 across the object OBJ and rotates outside the stationary circular component 200, on which the photon counting detectors PCD1 through PCDN are fixedly placed in a predetermined sparse manner.

In one implementation, the rotating portions 300 and 400 are integrally constructed as a single component such as the annular frame 102 to maintain the 180-degree angle between the X-ray source 101 and the detector unit 103 as they rotate about the object OBJ with a different radius. In an optional implementation, the rotating portions 300 and 400 are separate components but synchronously rotate to maintain the X-ray source 101 and the detector unit 103 in the fixedly opposed positions at 180 degrees across the object OBJ. Furthermore, the X-ray source 101 optionally travels a helical path as the object is moved in a predetermined direction that is perpendicular to the rotational plane of the rotating portion 300. Although it is not illustrated in the diagram, the rotating portions 300 and 400 are reversed in their diameters in another alternative embodiment. That is, although the source 101 and the detector unit 103 travel outside the sparsely placed photon counting detectors PCD1 through PCDN, the source 101 has a trajectory that is inside that of the detector unit 103 in the alternative embodiment while they travel at a diametrically fixed position with each other.

In the above exemplary embodiment, the X-ray source 101, the photon counting detectors (PCD) and the detector unit 103 collectively form three predetermined circular paths that differ in radius. The photon counting detectors (PCD) are sparsely placed along a first circular path around the object OBJ while at least one X-ray source 101 rotates along a second circular path around the object OBJ. Further, the detector unit 103 travels along a third circular path. The above exemplary embodiment illustrates that the second circular path is the largest and outside the first and third circular paths around the object OBJ.

Although it is not illustrated in a drawing, yet another alternative embodiment optionally changes the X-ray source 101 to travel on the same third circular path as the detector unit 103.

There are other alternative embodiments for placing the photon counting detectors (PCD) in a predetermined fourth-generation geometry in combination with the detector unit in a predetermined third-generation geometry in the CT scanner system according to the current invention. The X-ray source 101 is optionally a single energy source in certain embodiments. By the same token, an additional alternative embodiment optionally includes the X-ray source 101, which is configured to perform a kV-switching function for emitting X-ray at a predetermined high-level energy and a predetermined low-level energy. Furthermore, the radiation emitting source or the X-ray source 101 optionally modulates a combination of a radiation energy level and an intensity level over time.

As the X-ray source 101 and the detector unit 103 rotate around the object OBJ, the photon counting detectors PCDs and the detector unit 103 respectively detect the transmitted X-ray during the data acquisition. The photon counting detectors PCD1 through PCDN intermittently detect with a predetermined detector fan beam angle θB the X-ray that has been transmitted through the object OBJ and individually output a number of photons for each of predetermined energy components. On the other hand, the detector elements in the detector unit 103 continuously detect the X-ray that has been transmitted through the object OBJ and output the detected energy integration signals as the detector unit 103 rotates. Although the additional characteristics of the detector elements in the detector unit 103 will be later described in details, one implementation of the detector unit 103 has densely placed energy integrating detectors in a predetermined channel and segment directions on the detector unit surface.

FIG. 3 further discloses that since the source 101 travels outside the photon counting detectors PCD1 through PCDN, the X-ray is projected through openings or gaps between the sparsely placed photon counting detectors PCD1 through PCDN towards the object OBJ. Some portion of the emitted X-ray is blocked by certain ones of the sparsely placed photon counting detectors PCD1 through PCDN depending upon an angle with respect to the source 101. In other words, a certain portion of the emitted X-ray projects onto the back surface of some of the sparsely placed photon counting detectors PCD1 through PCDN at any given time as the source 101 is rotated around the predetermined trajectory 300. The remaining X-ray travels through the gap and reaches certain ones of the photon counting detectors PCD1 through PCDN, whose detecting surface is facing the source 101 and is substantially within the predetermined source fan beam angle θ A. Each of these photon counting detectors PCD1 through PCDN individually detects with the predetermined detector fan beam angle θ B. Furthermore, still some of the remaining X-ray travel an additional distance through another gap between certain ones of the photon counting detectors PCD1 through PCDN and reach the detector unit 103, whose detecting surface is substantially within the predetermined source fan beam angle θ A.

The above embodiments according to the current invention also provide a protective rear cover for each of the photon counting detectors PCD1 through PCDN that are irradiated from behind in a short distance. As the X-ray source 101 travels outside the first circular path of the sparsely placed photon counting detectors PCD1 through PCDN, the photon counting detectors PCD1 through PCDN are protected by the protective layer from the X-ray irradiation on the rear surface in order to substantially reduce undesirable effects as will be described with respect to FIG. 6.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique. In addition, the detector unit 103 also acquires another set of projection data, and the projection data from the detector unit 103 is used to generally improve image quality. In case that the detector unit 103 consists of energy integrating detectors (INTD) with anti-scatter grids, the projection data from the detector unit 103 is used to correct scatter on the projection data from the photon counting detectors (PCD). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 4:
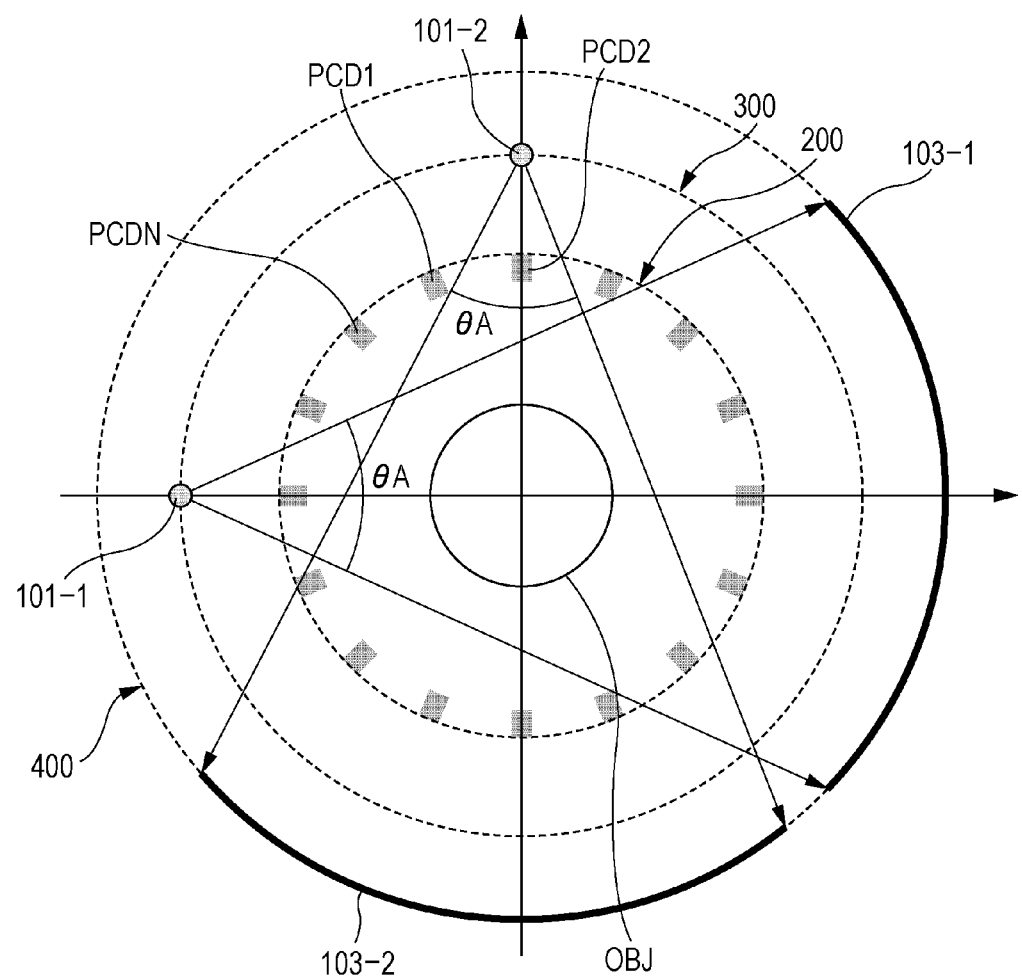
FIG. 4 is a diagram illustrating another embodiment for placing the photon counting detectors (PCD) in a predetermined fourth-generation geometry in combination with two X-ray sources and two detector units in a predetermined third-generation geometry in the CT scanner system according to the current invention.

Now referring to FIG. 4, a diagram illustrates another embodiment for placing the photon counting detectors (PCD) in a predetermined fourth-generation geometry in combination with two X-ray sources and two detector units in a predetermined third-generation geometry in the CT scanner system according to the current invention. The diagram merely illustrates a relative relationship among an object OBJ to be scanned, two radiation emitting sources or X-ray sources 101-1 and 101-2, two X-ray detector units 103-1 and 103-2 and the photon counting detectors PCD1 through PCDN in one exemplary embodiment. For the sake of simplicity, the diagram excludes other components and units that are necessary in acquiring and processing data as well as reconstructing an image based upon the acquired data.

As already described, approximately one hundred to three hundred photon counting detectors PCD1 through PCDN are generally utilized in certain embodiments. However, the above numerical range of the photon counting detectors is merely exemplary, and the claimed invention is not necessarily limited to any particular number of the photon counting detectors. In addition to the sparse photon counting detectors PCD1 through PCDN in the fourth-generation geometry, the exemplary embodiment of FIG. 4 now further includes at least two detector units 103-1 and 103-2 in a predetermined third-generation geometry in the CT scanner system according to the current invention. Although the detector units 103-1 and 103-2 are both energy integrating detectors in the embodiment, the two detectors are optionally different in other embodiments.

Still referring to FIG. 4, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. The circular component 200 also provides a gap between the two adjacent ones of the photon counting detectors PCD1 through PCDN, and these gaps allows the transmission of the X-ray without substantial interference. Although it is not illustrated in a drawing, an alternative embodiment optionally includes a predetermined component 200 that is substantially circular and non-circular such as polygonal along which the photon counting detectors PCD1 through PCDN are sparsely placed.

The two pairs of the X-ray sources 101-1, 101-2 and the detector units 103-1, 103-2 rotate around the object OBJ while the photon counting detectors PCD1 through PCDN remain stationary with respect to the object OBJ. For each pair, a rotating portion 400 respectively mounts the detector units 103-1 and 103-2 at a diametrically opposed position from the X-ray sources 101-1 and 101-2 across the object OBJ and rotates outside the stationary circular component 200, on which the photon counting detectors PCD1 through PCDN are fixedly placed in a predetermined sparse manner. Furthermore, a first pair of the X-ray source 101-1 and the detector unit 103-1 is mounted in a substantially perpendicular manner with respect to a second pair of the X-ray source 101-2 and the detector unit 103-2 in the gantry 100 in the above exemplary embodiment. Each of the X-ray sources 101-1 and 101-2 projects X-ray with a predetermined source fan beam angle θ A towards the object OBJ while the X-ray sources 101-1 and 101-2 rotate around the object OBJ outside the sparsely placed photon counting detectors PCD1 through PCDN.

In one implementation, the rotating portions 300 and 400 are integrally constructed as a single component such as the annular frame 102 to maintain the 180-degree angle between the X-ray sources 101-1, 101-2 and the detector units 103-1, 103-2 as they rotate about the object OBJ with a different radius. In an optional implementation, the rotating portions 300 and 400 are separate components but synchronously rotate to maintain the X-ray sources 101-1, 101-2 and the detector units 103-1, 103-2 in the fixedly opposed positions at 180 degrees across the object OBJ. Furthermore, the X-ray sources 101-1 and 101-2 optionally travel a helical path as the object is moved in a predetermined direction that is perpendicular to the rotational plane of the rotating portion 300. Although it is not illustrated in the diagram, the rotating portions 300 and 400 are reversed in their diameter in another alternative embodiment. That is, although the sources 101-1, 101-2 and the detector units 103-1 and 103-2 travel outside the sparsely placed photon counting detectors PCD1 through PCDN, the sources 101-1, 101-2 have a trajectory that is outside that of the detector units 103-1 and 103-2 while they travel at a diametrically fixed position with each other.

In the above exemplary embodiment, the X-ray sources 101-1, 101-2, the photon counting detectors (PCD) and the detector units 103-1, 103-2 collectively form three predetermined circular paths that differ in radius. The photon counting detectors (PCD) are sparsely placed along a first circular path around the object OBJ while the X-ray sources 101-1 and 101-2 rotate along a second circular path around the object OBJ. Further, the detector units 103-1 and 103-2 both travel along a third circular path. The above exemplary embodiment illustrates that the third circular path is the largest and outside the first and second circular paths around the object OBJ. Although it is not illustrated in a drawing, yet another alternative embodiment optionally changes the X-ray sources 101-1 and 101-2 to travel on the same third circular path as the detector units 103-1 and 103-2.

There are other alternative embodiments for placing the photon counting detectors (PCD) in a predetermined fourth-generation geometry in combination with two sources and two detector units in a predetermined third-generation geometry in the CT scanner system according to the current invention. At least one of the X-ray sources 101-1 and 101-2 is optionally a single energy source in certain embodiments. By the same token, an additional alternative embodiment optionally includes the X-ray sources 101-1 and or 101-2, which are configured to perform a kV-switching function for emitting X-ray at a predetermined high-level energy and a predetermined low-level energy. Furthermore, at least one of the radiation emitting sources or the X-ray sources 101-1 and 101-2 optionally modulates a combination of a radiation energy level and an intensity level over time.

As the X-ray sources 101-1, 101-2 and the detector units 103-1, 103-2 rotate around the object OBJ, the photon counting detectors (PCD) and the detector units 103-1, 103-2 respectively detect the transmitted X-ray during the data acquisition. The photon counting detectors PCD1 through PCDN intermittently detect with a predetermined detector fan beam angle θ B the X-ray that has been transmitted through the object OBJ and individually output a number of photons for each of predetermined energy components. On the other hand, the detector elements in the detector units 103-1 and 103-2 continuously detect the X-ray that has been transmitted through the object OBJ and output the detected energy integration signals as the detector units 103-1 and 103-2 rotate. Although the additional characteristics of the detector elements in the detector units 103-1 and 103-2 will be later described in details, one implementation of the detector units 103-1 and 103-2 has densely placed energy integrating detectors in a predetermined channel and segment directions on the detector unit surface.

FIG. 4 further discloses that since the X-ray sources 101-1 and 101-2 travel outside the photon counting detectors PCD1 through PCDN, the X-ray is projected through openings or gaps between the sparsely placed photon counting detectors PCD1 through PCDN towards the object OBJ. Some portion of the emitted X-ray is blocked by certain ones of the sparsely placed photon counting detectors PCD1 through PCDN depending upon an angle with respect to the X-ray sources 101-1 and 101-2. In other words, a certain portion of the emitted X-ray projects onto the back surface of some of the sparsely placed photon counting detectors PCD1 through PCDN at any given time as the X-ray sources 101-1 and 101-2 are rotated around the predetermined trajectory 300. The remaining X-ray travels through the gap and reaches certain ones of the photon counting detectors PCD1 through PCDN, whose detecting surface is facing the source 101-1 or 101-2 and is substantially within the predetermined source fan beam angle θ A. Each of these photon counting detectors PCD1 through PCDN individually detects with the predetermined detector fan beam angle θ B. Furthermore, still some of the remaining X-ray travel an additional distance through another gap between certain ones of the photon counting detectors PCD1 through PCDN and reach the detector unit 103-1 or 103-2, whose detecting surface is substantially within the predetermined source fan beam angle θ A.

The above embodiments according to the current invention also provide a protective rear cover for each of the photon counting detectors (PCD) that are irradiated from behind in a short distance. As the X-ray sources 101-1 and 101-2 travel outside the first circular path of the sparsely placed photon counting detectors PCD1 through PCDN, the photon counting detectors PCD1 through PCDN are protected by the protective layer from the X-ray irradiation on the rear surface in order to substantially reduce undesirable effects as will be described with respect to FIG. 6.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique. In addition, the detector units 103-1 and 103-2 respectively acquire another set of projection data, and the projection data from the detector units 103-1 and 103-2 is used to generally improve image quality. In case that the detector units 103-1 and 103-2 consist of integrating detectors (INTD) with anti-scatter grids, the projection data from the detector units 103-1 and 103-2 is used to correct scatter on the projection data from the photon counting detectors (PCD). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 5:
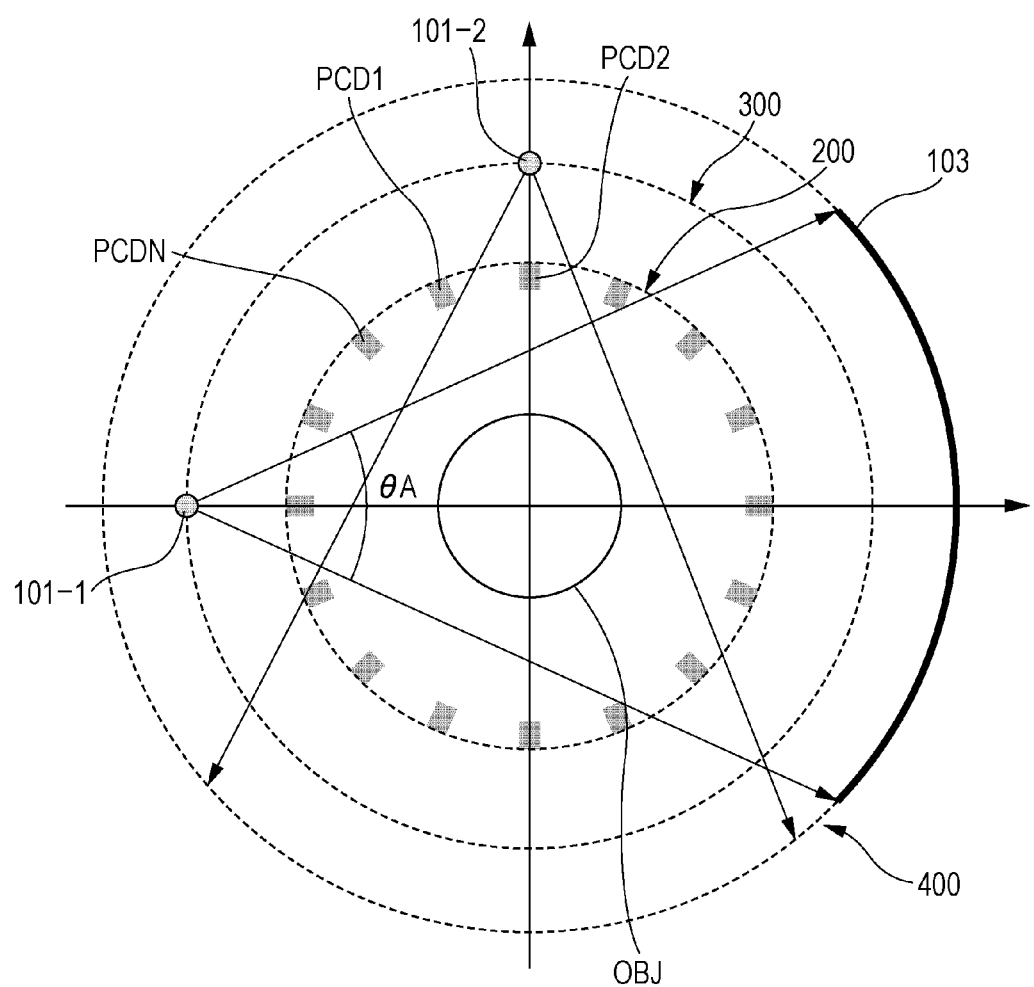
FIG. 5 is a diagram illustrating an alternative embodiment for placing the photon counting detectors (PCD) in a predetermined fourth-generation geometry in combination with two X-ray sources with only one corresponding detector unit a predetermined third-generation geometry in the CT scanner system according to the current invention.

Now referring to FIG. 5, a drawing illustrates an alternative embodiment for placing the photon counting detectors (PCD) in a predetermined fourth-generation geometry in combination with two X-ray sources with only one corresponding detector unit in a predetermined third-generation geometry in the CT scanner system according to the current invention. The diagram merely illustrates a relative relationship among an object OBJ to be scanned, two radiation emitting sources or X-ray sources 101-1 and 101-2, one X-ray detector units 103 and the photon counting detectors PCD1 through PCDN in one exemplary embodiment. For the sake of simplicity, the diagram excludes other components and units that are necessary in acquiring and processing data as well as reconstructing an image based upon the acquired data.

As already described, approximately one hundred to three hundred photon counting detectors PCD1 through PCDN are generally utilized in certain embodiments. However, the above numerical range of the photon counting detectors is merely exemplary, and the claimed invention is not necessarily limited to any particular number of the photon counting detectors. In addition to the sparse photon counting detectors PCD1 through PCDN in the fourth-generation geometry, the exemplary embodiment of FIG. 5 now further includes a single detector unit 103 in a predetermined third-generation geometry for detecting transmitted X ray substantially from either one of the two X-ray sources 101-1 and 101-2 in the CT scanner system according to the current invention.

Still referring to FIG. 5, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. The circular component 200 also provides a gap between the two adjacent ones of the photon counting detectors PCD1 through PCDN, and these gaps allows the transmission of the X-ray without substantial interference. Although it is not illustrated in a drawing, an alternative embodiment optionally includes a predetermined component 200 that is substantially circular and non-circular such as polygonal along which the photon counting detectors PCD1 through PCDN are sparsely placed.

The two X-ray sources 101-1,101-2 and the single detector unit 103 rotate around the object OBJ while the photon counting detectors PCD1 through PCDN are stationary with respect to the object OBJ. The rotating portion 400 mounts the detector unit 103 at a diametrically opposed position from the X-ray sources 101-1 across the object OBJ and rotates outside the stationary circular component 200, on which the photon counting detectors PCD1 through PCDN are fixedly placed in a predetermined sparse manner. Furthermore, the pair of the X-ray source 101-1 and the detector unit 103 is mounted in a substantially perpendicular manner with respect to the central projection direction of the X-ray source 101-2 on a first rotating portion 300 such as the annular frame 102 in the gantry 100 in the above exemplary embodiment. Each of the X-ray sources 101-1 and 101-2 projects X-ray with a predetermined source fan beam angle θ A towards the object OBJ while the X-ray sources 101-1 and 101-2 rotate around the object OBJ outside the sparsely placed photon counting detectors PCD1 through PCDN.

In one implementation, the rotating portions 300 and 400 are integrally constructed as a single component such as the annular frame 102 to maintain the 180-degree angle between the X-ray sources 101-1 and the detector unit 103 as they rotate about the object OBJ with a different radius. In an optional implementation, the rotating portions 300 and 400 are separate components but synchronously rotate to maintain the X-ray source 101-1 and the detector unit 103 in the fixedly opposed positions at 180 degrees across the object OBJ. Furthermore, the X-ray sources 101-1 and 101-2 optionally travel a helical path as the object is moved in a predetermined direction that is perpendicular to the rotational plane of the rotating portion 300. Although it is not illustrated in the diagram, the rotating portions 300 and 400 are reversed in their diameter in another alternative embodiment. That is, although the sources 101-1, 101-2 and the detector unit 103 travel outside the sparsely placed photon counting detectors PCD1 through PCDN, the sources 101-1, 101-2 have a trajectory that is outside that of the detector unit 103.

In the above exemplary embodiment, the X-ray sources 101-1, 101-2, the photon counting detectors (PCD) and the detector unit 103 collectively form three predetermined circular paths that differ in radius. The photon counting detectors (PCD) are sparsely placed along a first circular path around the object OBJ while the X-ray sources 101-1 and 101-2 rotate along a second circular path around the object OBJ. Further, the detector unit 103 travels along a third circular path. The above exemplary embodiment illustrates that the third circular path is the largest and outside the first and second circular paths around the object OBJ. Although it is not illustrated in a drawing, yet another alternative embodiment optionally changes the X-ray sources 101-1 and 101-2 to travel on the same third circular path as the detector unit 103.

There are other alternative embodiments for placing the photon counting detectors (PCD) in a predetermined fourth-generation geometry in combination with two sources and one detector unit in a predetermined third-generation geometry in the CT scanner system according to the current invention. At least one of the X-ray sources 101-1 and 101-2 is optionally a single energy source in certain embodiments. By the same token, an additional alternative embodiment optionally includes the X-ray sources 101-1 and or 101-2, which are configured to perform a kV-switching function for emitting X-ray at a predetermined high-level energy and a predetermined low-level energy. Furthermore, at least one of the radiation emitting sources or the X-ray sources 101-1 and 101-2 optionally modulates a combination of a radiation energy level and an intensity level over time.

As the X-ray sources 101-1, 101-2 and the detector unit 103 rotate around the object OBJ, the photon counting detectors (PCD) and the detector unit 103 respectively detect the transmitted X-ray during the data acquisition. The photon counting detectors PCD1 through PCDN intermittently detect with a predetermined detector fan beam angle θ B the X-ray that has been transmitted through the object OBJ and individually output a number of photons for each of predetermined energy components. Because there are two X-ray sources 101-1 and 101-2, the photon counting detectors PCD1 through PCDN output two sets of a number of photons for each of predetermined energy components. The two sets of the spectral data are varied depending upon the angle between the two X-ray sources 101-1 and 101-2.

On the other hand, the detector elements in the detector unit 103 continuously detect the X-ray that has been transmitted through the object OBJ and output the detected energy integration signals as the detector unit 103 rotates. Although the additional characteristics of the detector elements in the detector unit 103 will be later described in details, one implementation of the detector unit 103 has densely placed integrating detectors in a predetermined channel and segment directions on the detector unit surface.

FIG. 5 further discloses that since the X-ray sources 101-1 and 101-2 travel outside the photon counting detectors PCD1 through PCDN, the X-ray is projected through openings or gaps between the sparsely placed photon counting detectors PCD1 through PCDN towards the object OBJ. Some portion of the emitted X-ray is blocked by certain ones of the sparsely placed photon counting detectors PCD1 through PCDN depending upon an angle with respect to the X-ray sources 101-1 and 101-2. In other words, a certain portion of the emitted X-ray projects onto the back surface of some of the sparsely placed photon counting detectors PCD1 through PCDN at any given time as the X-ray sources 101-1 and 101-2 are rotated around the predetermined trajectory 300. The remaining X-ray travels through the gap and reaches certain ones of the photon counting detectors PCD1 through PCDN, whose detecting surface is facing the source 101-1 or 101-2 and is substantially within the predetermined source fan beam angle θ A. Each of these photon counting detectors PCD1 through PCDN individually detects with the predetermined detector fan beam angle θ B. Furthermore, still some of the remaining X-ray travel an additional distance through another gap between certain ones of the photon counting detectors PCD1 through PCDN and reach the detector unit 103, whose detecting surface is substantially within the predetermined source fan beam angle θ A.

The above alternative embodiments optionally provide a protective rear cover for each of the photon counting detectors PCD1 through PCDN that are irradiated from behind in a short distance. As the X-ray sources 101-1 and 101-2 travel outside the first circular path of the sparsely placed photon counting detectors PCD1 through PCDN, the photon counting detectors PCD1 through PCDN are protected by the protective layer from the X-ray irradiation on the rear surface in order to substantially reduce undesirable effects as will be described with respect to FIG. 6.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique. Furthermore, the above described embodiment acquires two sets of the sparse view projection data due to a pair of the X-ray sources 101-1 and 101-2. In addition, the detector unit 103 acquires another set of projection data, and the projection data from the detector unit 103 is used to generally improve image quality. In case that the detector unit 103 consists of energy integrating detectors (INTD) with anti-scatter grids, the projection data from the detector unit 103 is used to correct scatter on the projection data from the photon counting detectors (PCDs). In the above alternative embodiments, the integrating detectors (INTD) optionally need to be calibrated in view of X-ray transmission through the predetermined circular component 200 and some of the photon counting detectors (PCD). In acquiring the projection data, a sampling on the source trajectory is optionally made dense in order to enhance spatial resolution.

Figure 6:
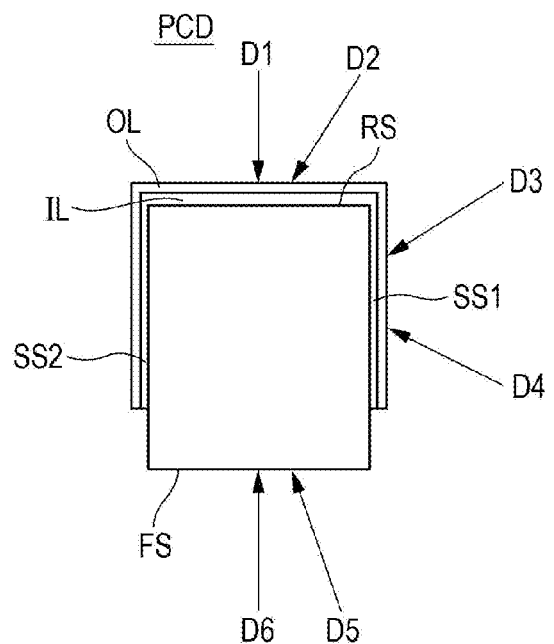
FIG. 6 is a diagram illustrating an embodiment of a protect layer or cover for the photon counting detectors (PCD) in a predetermined fourth-generation geometry in the CT scanner system according to the current invention.

Now referring to FIG. 6, a diagram illustrates an embodiment of a protect layer or cover for the energy differentiating detector such as a photon counting detector PCD or a semiconductor direct conversion detector in a predetermined fourth-generation geometry in the CT scanner system according to the current invention. The diagram illustrates a cross sectional view of the photon counting detectors PCD, whose rear surface RS is illustrated above the front surface FS. A first side surface SS1 is on the right while a second side surface SS2 is on the left. An outer surface in the current application is defined to include both the rear surface RS and the side surfaces SS1 and SS2. Although an inner surface is not referenced in the diagram, it is also defined that the inner surface such as in a detecting layer exists inside the photon counting detector PCD and is distinguished from the outer surface.

In general, the front surface FS is designed to have a detecting surface through which X-ray radiation is received for detecting photons in a detecting layer in the photon counting detector PCD. On the other hand, although the rear surface RS and the side surfaces SS1 and SS2 are not designed to have a detecting surface, a certain level of X-ray radiation may adversely reach the detecting layer through the rear surface RS or the side surfaces SS1 and SS2. Thus, a photon count may be adversely affected due to the unintended measurements. Consequently, undesirable effects are caused during reconstruction by the inaccurate photon counts that are affected by the unintended measurements through the rear surface RS or the side surfaces SS1 and SS2. In order to substantially reduce the undesirable effects in the fourth-generation geometry, one embodiment of the photon counting detectors provides the protective layers to shield the radiation according to the current invention.

Still referring to FIG. 6, the diagram further illustrates two protective layers or covers in one embodiment of the photon counting detectors according to the current invention. The embodiment includes an inner layer IL, which is placed directly upon a substantially entire portion of the rear surface RS and a certain predetermined portion of the side surfaces SS1 and SS2. The embodiment also includes an outer layer OL, which is located directly on top of the inner layer IL and covers the substantially same portion of the rear surface RS and the side surfaces SS1 and SS2 as the inner layer IL. The extent of shielding by the outer layer OL and or the inner layer IL is not limited to the above described extent over the rear surface RS and the side surfaces SS1 and SS2 in other embodiments according to the current invention. The side surfaces SS1 and SS2 are either fully or partially shielded by the inner layer IL and or the outer layer OL. In other embodiments, the extent of the protection differs between the inner layer IL and the outer layer OL. Furthermore, an alternative embodiment also includes a single layer for protecting the photon counting detector PCD.

In the embodiments as described with respect to FIGS. 1 through 5, the X-ray is emitted from the X-ray source 101, 101-1 or 101-2, which travels over a predetermined path that is radially outside of the sparsely located photon counting detectors the photon counting detectors PCD1 through PCDN. Each of the photon counting detectors the photon counting detectors PCD1 through PCDN is fixedly positioned, and the front surface FS is facing radially inward towards the object OBJ to be scanned. That is, when the X-ray source 101, 101-1 or 101-2 is located behind a particular one of the photon conducting detectors PCD1 through PCDN, X-ray is radiated from the rear towards the rear surface RS along a first direction D1 or a second direction D2 as illustrated in FIG. 6. The two protective layers OL and IL protect the photon conducting detector PCD from X-ray that is projected in a relatively short distance as the X-ray source is located substantially behind the photon conducting detector PCD.

Referring back to FIG. 6, the X-ray source travels in the clockwise direction along a predetermined path outside the sparsely placed photon conducting detector PCDs. As the X-ray source travels, certain rays of the X-ray are projected towards the photon conducting detector PCD onto the side surface SS1 along a third direction D3 or a fourth direction D4. The two protective layers OL and IL still protect the photon conducting detector PCD from the X-ray that is projected in a relatively short distance as the X-ray source is located substantially near the photon conducting detector PCD. At the same time, the above described unintended photon count is substantially reduced in the output from the photon conducting detector PCD.

Subsequently, as the X-ray source further travels in the clockwise direction along the predetermined path outside the sparsely placed photon conducting detector PCDs, certain rays of the X-ray are now projected onto the front surface FS along a fifth direction D5 or a sixth direction D6 as illustrated in FIG. 6. These rays are projected from the X-ray source at a substantially diametrically opposite position across the object across the photon conducting detector PCD. In other words, the rays reach the front surface FS after travelling through at least a gap between the two adjacent ones of the photon conducting detectors PCDs that are located near the X-ray source. Finally, photons are counted in the detecting layer in the photon conducting detector PCD for an output signal.

The two layers have distinct properties for shielding the embodiment of the photon counting detector according to the current invention. In one embodiment, the outer layer OL is made of at least a predetermined high-Z material, which substantially absorbs the X-ray radiation. On the other hand, the inner layer IL is made of at least a predetermined low-Z material, which absorbs characteristic X-rays that is emitted from the outer high-Z shielding layer OL. The characteristic X-rays that is emitted from the inner low-Z shielding layer IL are substantially low in energy that is approximately less than 10 keV and are effectively eliminated by the photon counting detector PCD.

Figure 7:
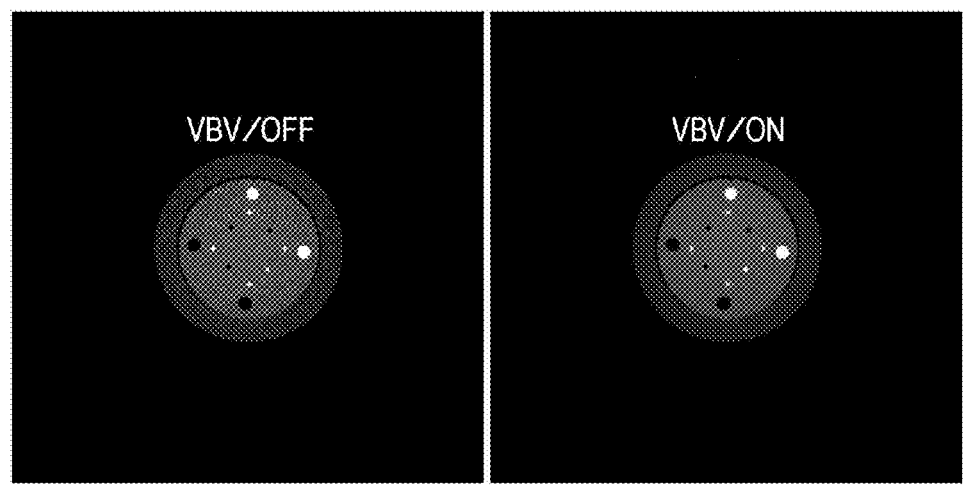
FIG. 7 illustrates an effect of a view-by-view correction on the exemplary image reconstructed from the data acquired by embodiments for placing the photon counting detectors (PCD) in a predetermined fourth-generation geometry in combination with a detector unit in a predetermined third-generation geometry in the CT scanner system according to the current invention.

Now referring to FIG. 7, an effect of a view-by-view correction is shown in the exemplary image reconstructed from the data acquired by embodiments for placing the photon counting detectors (PCD) in a predetermined fourth-generation geometry in combination with a detector unit in a predetermined third-generation geometry in the CT scanner system according to the current invention. A view-by-view correction is necessary for the third-generation detector in the embodiments as described with respect to FIGS. 3 through 5. In general, the view-by-view correction for the measured data from the energy integrating detector is necessitated by the fourth-generation geometry of the photon counting detectors. Since X-ray source 101, 101-1 or 101-2 travels over a predetermined path that is radially outside of the sparsely located photon counting detectors, the fixedly positioned photon counting detectors PCD1 through PCDN block some of the emitted X-ray depending upon the angle of the X-ray source with respect to the photon counting detectors PCD1 through PCDN.

Because of the blockage, the air calibration is necessary depending upon the view angle. In some detail, air scan data is collected for every element of the energy integrating detector in the above described embodiments using the same scan parameters as the future actual scan for image reconstruction. The air scan may be performed either at a predetermined calibration interval or at the beginning or end of the actual scan without an object or a patient. After the actual scan, the above described air scan data is deducted from the actually scanned energy integration data, usually in log scale. For an improved view-by-view correction, the air calibration scan data may be determined based upon an average from multiple air scans. The calibration is not necessarily limited to the air calibration and includes other calibrations such as wateror any known phantom calibrations.

FIG. 7 compares the effect in two images with (VBV/ON) or without (VBV/OFF) the view-by-view correction. The image on the right as labeled VBV/ON has been reconstructed with the view-by-view correction. The image on the left as labeled VBV/OFF has been reconstructed without the view-by-view correction.

By the same token, the spectral data is optionally corrected for each view based upon blockage of the radiation caused by the energy differentiating detectors. Since the X-ray source travels outside the sparsely placed photon counting detectors and the X-ray travels between the two adjacent ones of the photon counting detectors before reaching the detecting surface of a particular photon counting detector, certain blockage by other photon counting detectors is optionally taken into account to corrected the acquired spectral data.

Figure 8:
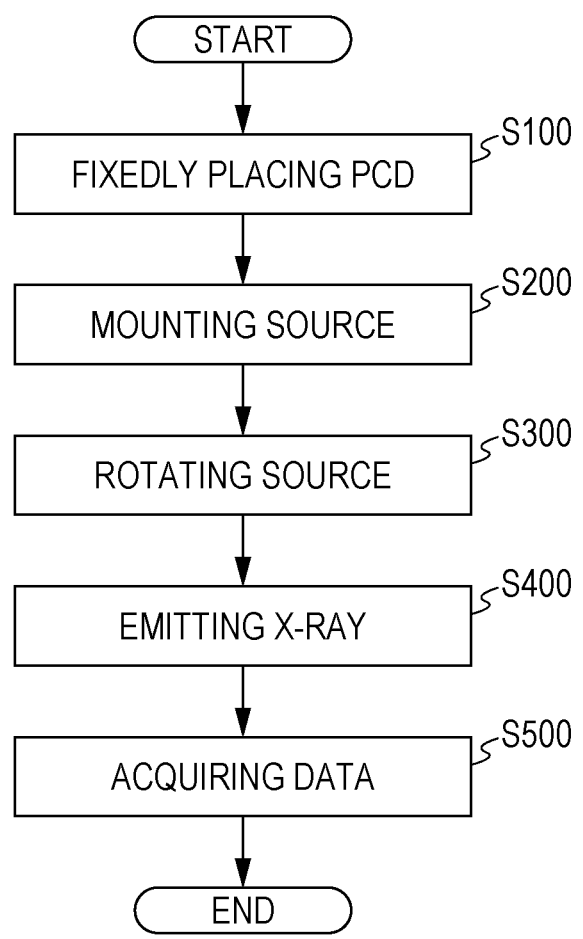
FIG. 8 is a flow chart illustrating steps or acts involved in a process or method of acquiring data for spectral CT using sparse photon counting detectors according to the current invention.

Now referring to FIG. 8, a flow chart illustrates steps or acts involved in a process or method of acquiring data for spectral CT using sparse photon counting detectors according to the current invention. The flow chart merely depicts the acts or steps involving an object to be scanned, an X-ray source and the photon counting detectors in one exemplary embodiment. For the sake of simplicity, the flow chart excludes the acts or steps involving other components and units that are necessary in acquiring and processing data as well as reconstructing an image based upon the acquired data. In general, the photon counting detectors are each a device and output a photon count for each of predetermined energy components.

In a step S100, approximately one hundred to three hundred photon counting detectors are sparsely placed on a stationary component around an object to be scanned in a predetermined fourth-generation geometry such as a first circular path around the object. The circular component remains stationary with respect to the object and fails to rotate during the data acquisition. In one embodiment, the photon counting detectors are fixedly placed at predetermined equidistant positions while in another embodiment the photon counting detectors are fixedly placed at predetermined non-equidistant positions. The above numerical range of the photon counting detectors is merely exemplary, and the claimed invention is not necessarily limited to any particular number of the photon counting detectors.

In a step S200, at least a single X-ray source is mounted on a rotating portion such as the annular frame in the gantry. The annular frame is a second circular path also around the object. In one process, the first circular path along which the photon counting detectors are sparsely placed is smaller and inside the second circular path on which the X-ray source is mounted. In another process, the second circular path for the X-ray source is optionally smaller and inside the first circular path of the sparsely placed photon counting detectors around the object to practice the current invention. In yet another process, a plurality of the X-ray sources is mounted on the rotating portion at a predetermined angle with each other.

In a step S300, the X-ray source rotates around the object. In one process, the X-ray source rotates around the object inside the sparsely placed photon counting detectors in the step S300. In another process, the X-ray source rotates around the object outside the sparsely placed photon counting detectors in the step S300, in which an additional step is optionally needed to protect the photon counting detectors that receive the X-ray from the behind in a short distance.

In a step S400, the X-ray source emits X-ray with a predetermined source fan beam angle towards the object while it simultaneously rotates in the step S300 in one process. At least one of the X-ray sources is optionally a single energy source in a certain process. By the same token, an alternative process optionally includes the X-ray source, which is configured to perform a kV-switching function for emitting X-ray at a predetermined high-level energy and a predetermined low-level energy in the step S400. Furthermore, at least one radiation emitting source or the X-ray source optionally modulates a combination of a radiation energy level and an intensity level over time.

In a step S500, the photon counting detectors individually detect with a predetermined detector fan beam angle the X-ray that has been transmitted through the object in the step S400. The photon counting detectors output a photon count for each of predetermined energy components. Thus, the step S500 acquires data.

The above described steps or acts of the process are merely illustrative, and the process of acquiring data operates in different manners for spectral CT using sparse photon counting detectors according to the current invention. Although the steps S100 through S500 are described in a single sequence of events or acts in one process, some of the steps in the process are repetitively performed while others are only initially performed. Furthermore, some steps of the process are simultaneously performed during the repetitive performance.

Figure 9:
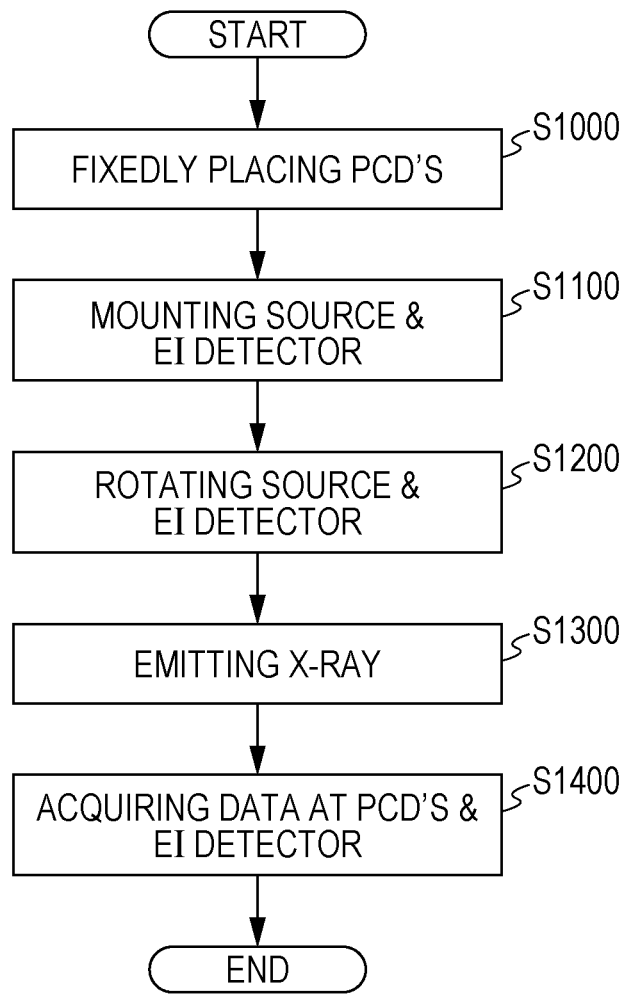
FIG. 9 is a flow chart illustrating steps or acts involved in a process or method of acquiring data for spectral CT using a combination of sparse photon counting detectors and integrating detectors according to the current invention.

Now referring to FIG. 9, a flow chart illustrates steps or acts involved in a process or method of acquiring data for spectral CT using a combination of sparsely placed energy differentiating detectors and at least one energy integrating detector according to the current invention. The flow chart merely depicts the acts or steps involving an object to be scanned, an X-ray source, the energy integrating detectors and the energy differentiating detectors such as photon counting detectors in one exemplary embodiment. For the sake of simplicity, the flow chart excludes the acts or steps involving other components and units that are necessary in acquiring and processing data as well as reconstructing an image based upon the acquired data. In general, the photon counting detectors are each a device and output a photon count for each of predetermined energy components.

In a step S1000, approximately one hundred to three hundred photon counting detectors are sparsely placed on a stationary component around an object to be scanned in a predetermined fourth-generation geometry such as a first circular path around the object. The circular component remains stationary with respect to the object and fails to rotate during the data acquisition. In one embodiment, the photon counting detectors are fixedly placed at predetermined equidistant positions while in another embodiment the photon counting detectors are fixedly placed at predetermined non-equidistant positions. The above numerical range of the photon counting detectors is merely exemplary, and the claimed invention is not necessarily limited to any particular number of the photon counting detectors.

In a step S1100, an X-ray source and a detector unit are mounted on a rotating portion. At least a single X-ray source is mounted on a first rotating portion such as the annular frame in the gantry. The annular frame is a second circular path also around the object. In one process, the first circular path along which the photon counting detectors are sparsely placed is smaller and inside the second circular path on which the X-ray source is mounted. In another process, the second circular path for the X-ray source is optionally smaller and inside the first circular path of the sparsely placed photon counting detectors around the object to practice the current invention. In yet another process, a plurality of the X-ray sources is mounted on the rotating portion at a predetermined angle with each other.

Also in the step S1100, the detector unit is mounted on a second rotating portion in the third-generation geometry outside the sparsely placed photon counting detectors in the step S1000. In one process, the detector unit consists of a plurality of energy integrating detector elements. In one process, the first rotating portion and the second rotating portions are formed in an integral manner. In another process, the first rotating portion and the second rotating portions are separately formed and independently rotatable.

In a step S1200, the X-ray source and the detector unit rotate around the object. In one process, the X-ray source rotates around the object outside the sparsely placed photon counting detectors in the step S1200, in which an additional step is optionally needed to protect the photon counting detectors that receive the X-ray from the behind in a short distance. In another process, the X-ray source rotates around the object inside the sparsely placed photon counting detectors in the step S1200. In the step S1200, the detector unit also rotates around the object. In one process, the detector unit rotates around the object outside the sparsely placed photon counting detectors in the step S1000.

In a step S1300, the X-ray source emits X-ray with a predetermined source fan beam angle towards the object while it simultaneously rotates in the step S1200 in one process. At least one of the X-ray sources is optionally a single energy source in a certain process. By the same token, an alternative process optionally includes the X-ray source, which is configured to perform a kV-switching function for emitting X-ray at a predetermined high-level energy and a predetermined low-level energy in the step S1300. Furthermore, at least one radiation emitting source or the X-ray source optionally modulates a combination of a radiation energy level and an intensity level over time.

In a step S1400, the photon counting detectors individually detect with a predetermined detector fan beam angle the X-ray that has been transmitted through the object in the step S1300. The photon counting detectors output a photon count for each of predetermined energy components. In the step S1400, the detector unit also detects the X-ray that has been transmitted through the object in the step S1300. Thus, the step S1400 acquires data.

The above described steps or acts of the process are merely illustrative, and the process of acquiring data operates in different manners for spectral CT using sparse photon counting detectors according to the current invention. Although the steps S1000 through S1400 are described in a single sequence of events or acts in one process, some of steps in the process are repetitively performed while others are only initially performed. Furthermore, some steps of the process are simultaneously performed during the repetitive performance.

Figure 10:
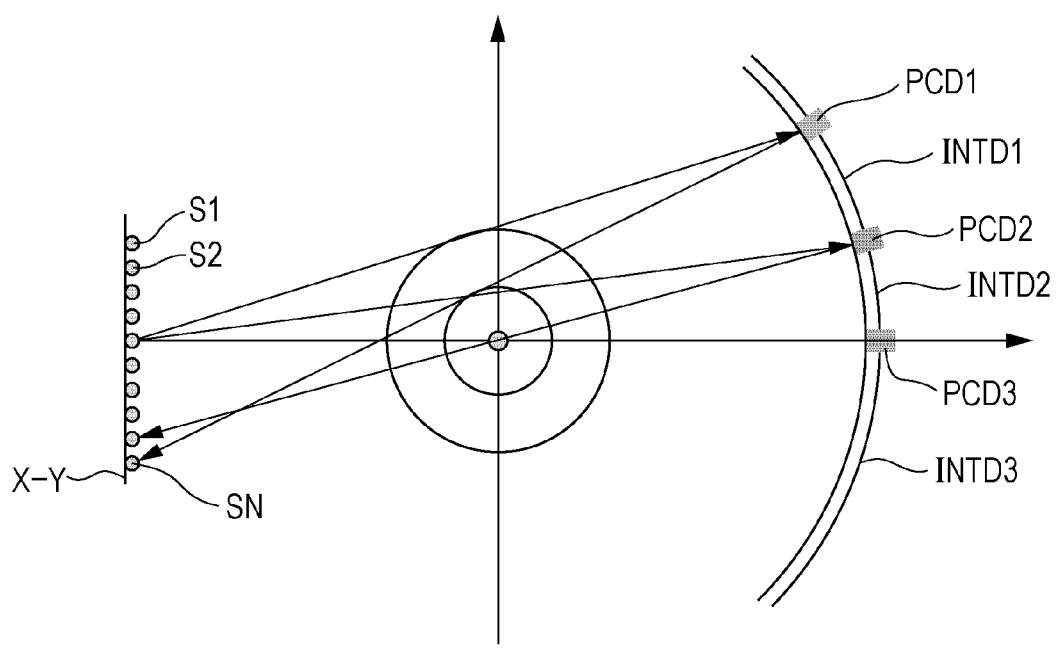
FIG. 10 is a diagram illustrating sparsely placed photon counting detectors and integrating detectors in combination with fly focal spot in the CT scanner system according to the current invention.

Now referring to FIG. 10, a diagram illustrates sparsely placed energy differentiating detectors such as photon counting detectors and energy integrating detectors in combination with fly focal spot in the CT scanner system according to the current invention. On the right hand side, the diagram partially illustrates sparsely placed photon counting detectors PCD1 through PCD3 and the integrating detectors INTD1 and INTD2 that are respectively placed between the two adjacent photon counting detectors PCD1 through PCD3 on the same surface with no tunnel without anti-scatter grid on the energy integrating detectors. In the center of the diagram, the two concentric circles and a concentric center respectively signify the photon counting detectors PCD1 through PCD3. On the left hand side, the diagram partially illustrates the projections from the source to the photon counting detectors PCD1 through PCD3. The source position is optionally moved by fly focal spots on a predetermined X-Y plane in one embodiment. The source position is optionally moved by fly focal spots in the Z-direction in addition to a predetermined X-Y plane in another embodiment. The tangential points on the central circles indicate the measured data.

Still referring to FIG. 10, data sufficiency improves with fly focal spot. Sparse photon counting detectors (PCD) with a fixed focal spot may not provide sufficient data for dual energy (DE) reconstruction. On the other hand, fly focal spot combined with sparse photon counting detectors (PCD) optionally provide sufficient data. Furthermore, data from integrating detectors (INTD) are redundant with fly focal spot for optionally improving image quality in terms of noise and resolution. Software correction is optionally needed to reduce scatter in the acquired data. In an iterative reconstruction, software scatter correction proves to be accurate.

Figure 11:
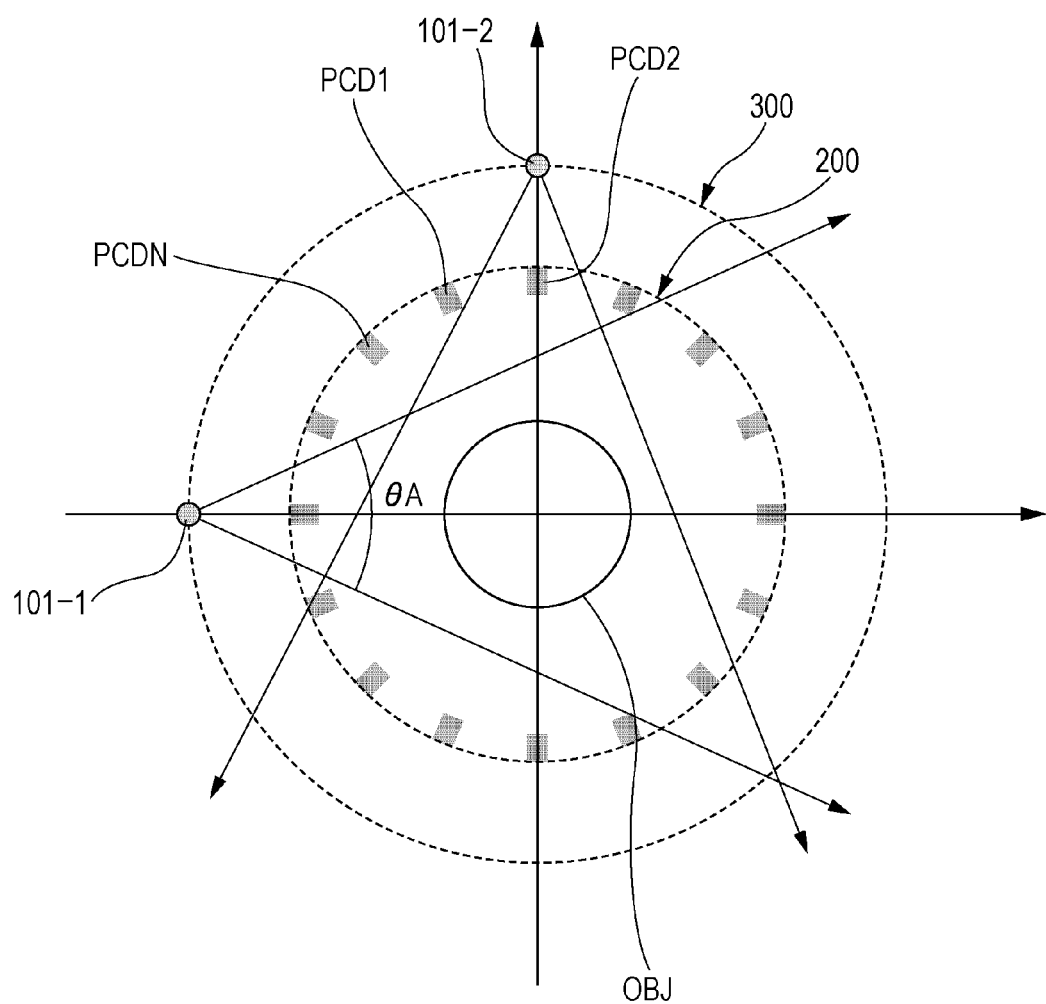
FIG. 11 is a diagram illustrating an alternative embodiment for placing the photon counting detectors (PCD) in a predetermined fourth-generation geometry in combination with two X-ray sources without any detector unit in third-generation geometry in the CT scanner system according to the current invention.

FIG. 11 is a diagram illustrating an alternative embodiment for placing the photon counting detectors (PCD) in a predetermined fourth-generation geometry in combination with two X-ray sources without any detector unit in third-generation geometry in the CT scanner system according to the current invention. The diagram merely illustrates a relative relationship among an object OBJ to be scanned, two radiation emitting sources or X-ray sources 101-1 and 101-2 and the photon counting detectors PCD1 through PCDN in one exemplary embodiment. For the sake of simplicity, the diagram excludes other components and units that are necessary in acquiring and processing data as well as reconstructing an image based upon the acquired data.

As already described, approximately one hundred to three hundred photon counting detectors PCD1 through PCDN are generally utilized in certain embodiments. However, the above numerical range of the photon counting detectors is merely exemplary, and the claimed invention is not necessarily limited to any particular number of the photon counting detectors.

Still referring to FIG. 11, one embodiment includes a predetermined number of the photon counting detectors (PCD), which are sparsely placed around the object OBJ in a predetermined geometry such as a circle. For example, the photon counting detectors PCD1 through PCDN are fixedly placed on a predetermined circular component 200 in the gantry 100. Furthermore, the photon counting detectors PCD1 through PCDN are fixedly placed on the circular component 200 at predetermined equidistant positions in one embodiment. In another embodiment, the photon counting detectors PCD1 through PCDN are fixedly placed on the circular component 200 at predetermined non-equidistant positions. The circular component 200 remains stationary with respect to the object OBJ and fails to rotate during the data acquisition. The circular component 200 also provides a gap between the two adjacent ones of the photon counting detectors PCD1 through PCDN, and these gaps allows the transmission of the X-ray without substantial interference. Although it is not illustrated in a drawing, an alternative embodiment optionally includes a predetermined component 200 that is substantially circular and non-circular such as polygonal along which the photon counting detectors PCD1 through PCDN are sparsely placed.

The two X-ray sources 101-1,101-2 rotate around the object OBJ while the photon counting detectors PCD1 through PCDN are stationary with respect to the object OBJ. The rotating portion 300 mounts the X-ray sources 101-1, 101-2 and rotates outside the stationary circular component 200, on which the photon counting detectors PCD1 through PCDN are fixedly placed in a predetermined sparse manner. Furthermore, the X-ray source 101-1 is mounted in a substantially perpendicular manner with respect to the central projection direction of the X-ray source 101-2 on a first rotating portion 300 such as the annular frame 102 in the gantry 100 in the above exemplary embodiment. The relative angle between the two X-ray sources 101-1,101-2 is not limited to 90 degrees in other embodiments. Each of the X-ray sources 101-1 and 101-2 projects X-ray with a predetermined source fan beam angle θ A towards the object OBJ while the X-ray sources 101-1 and 101-2 rotate around the object OBJ outside the sparsely placed photon counting detectors PCD1 through PCDN.

In one implementation, the X-ray sources 101-1 and 101-2 optionally travel a helical path as the object is moved in a predetermined direction that is perpendicular to the rotational plane of the rotating portion 300. Although the sources 101-1, 101-2 travel outside the sparsely placed photon counting detectors PCD1 through PCDN, the sources 101-1, 101-2 have a trajectory that is different with each other. There are other alternative embodiments for placing the photon counting detectors (PCD) in a predetermined fourth-generation geometry in combination with two sources in the CT scanner system according to the current invention. At least one of the X-ray sources 101-1 and 101-2 is optionally a single energy source in certain embodiments. By the same token, an additional alternative embodiment optionally includes the X-ray sources 101-1 and or 101-2, which are configured to perform a kV-switching function for emitting X-ray at a predetermined high-level energy and a predetermined low-level energy. Furthermore, at least one of the radiation emitting sources or the X-ray sources 101-1 and 101-2 optionally modulates a combination of a radiation energy level and an intensity level over time.

As the X-ray sources 101-1, 101-2 rotate around the object OBJ and the photon counting detectors (PCD) detect the transmitted X-ray during the data acquisition. The photon counting detectors PCD1 through PCDN intermittently detect with a predetermined detector fan beam angle θ B the X-ray that has been transmitted through the object OBJ and individually output a number of photons for each of predetermined energy components. Because there are two X-ray sources 101-1 and 101-2, the photon counting detectors PCD1 through PCDN output two sets of a number of photons for each of predetermined energy components. The two sets of the spectral data are varied depending upon the angle between the two X-ray sources 101-1 and 101-2.

FIG. 11 further discloses that since the X-ray sources 101-1 and 101-2 travel outside the photon counting detectors PCD1 through PCDN, the X-ray is projected through openings or gaps between the sparsely placed photon counting detectors PCD1 through PCDN towards the object OBJ. Some portion of the emitted X-ray is blocked by certain ones of the sparsely placed photon counting detectors PCD1 through PCDN depending upon an angle with respect to the X-ray sources 101-1 and 101-2. In other words, a certain portion of the emitted X-ray projects onto the back surface of some of the sparsely placed photon counting detectors PCD1 through PCDN at any given time as the X-ray sources 101-1 and 101-2 are rotated around the predetermined trajectory 300. The remaining X-ray travels through the gap and reaches certain ones of the photon counting detectors PCD1 through PCDN, whose detecting surface is facing the source 101-1 or 101-2 and is substantially within the predetermined source fan beam angle θ A. Each of these photon counting detectors PCD1 through PCDN individually detects with the predetermined detector fan beam angle θ B.

The above alternative embodiments optionally provide a protective rear cover for each of the photon counting detectors PCD1 through PCDN that are irradiated from behind in a short distance. As the X-ray sources 101-1 and 101-2 travel outside the first circular path of the sparsely placed photon counting detectors PCD1 through PCDN, the photon counting detectors PCD1 through PCDN are protected by the protective layer from the X-ray irradiation on the rear surface in order to substantially reduce undesirable effects as will be described with respect to FIG. 6.

In general, the photon counting detectors PCD1 through PCDN are sparsely positioned along the circular component 200. Although the photon counting detectors PCD1 through PCDN acquire sparse view projection data, the acquired projection data is sufficient for at least dual energy (DE) reconstruction with a certain sparse view reconstruction technique. Furthermore, the above described embodiment acquires two sets of the sparse view projection data due to a pair of the X-ray sources 101-1 and 101-2.

It is to be understood, however, that even though numerous characteristics and advantages of the present invention have been set forth in the foregoing description, together with details of the structure and function of the invention, the disclosure is illustrative only, and that although changes may be made in detail, especially in matters of shape, size and arrangement of parts, as well as implementation in software, hardware, or a combination of both, the changes are within the principles of the invention to the full extent indicated by the broad general meaning of the terms in which the appended claims are expressed.

What is claimed is:

1. A method of reconstructing an image, comprising:
    fixedly placing a predetermined number of energy differentiating detectors around an object along a first path;
    moving at least one radiation emitting source along a predetermined second path outside the first path while continuously emitting radiation towards the object, the fixedly placed energy differentiating detectors being stationary on the first path with respect to the moving radiation emitting source;
    detecting spectral data at the energy differentiating detectors;
    reconstructing an image based upon the spectral data; and
    providing an outer high-Z material shielding layer and an inner low-Z material shielding layer on at least an outer surface of each of the energy differentiating detectors, the outer surface being closer to the radiation emitting source than an inner surface of the energy differentiating detectors.

2. The method of reconstructing an image according to claim 1 further comprising additional steps of:
    moving at least one energy integrating detector for detecting intensity data along a predetermined third path around the object; and
    reconstructing the image based upon the intensity data and the spectral data.

3. The method of reconstructing an image according to claim 2 wherein the radiation emitting source modulates a combination of a radiation energy level and an intensity level over time.

4. The method of reconstructing an image according to claim 1 further comprising an additional step of correcting intensity data based upon blockage of the radiation caused by the energy differentiating detectors.

5. The method of reconstructing an image according to claim 1 further comprising an additional step of correcting the spectral data based upon blockage of the radiation caused by the energy differentiating detectors.

6. The method of reconstructing an image according to claim 4 whereas the correcting step is based upon view-by-view calibration.

7. The method of reconstructing an image according to claim 1 wherein the energy differentiating detectors include photon counting detectors.

8. The method of reconstructing an image according to claim 1 wherein the energy differentiating detectors include semiconductor direct conversion detectors.

9. The method of reconstructing an image according to claim 1 wherein the energy differentiating detectors are sparsely placed within a predetermined range of less than 150 detectors.

10. The method of reconstructing an image according to claim 1 wherein the object moves along a predetermined direction while the spectral data is being collected.

11. The method of reconstructing an image according to claim 1 wherein at least the one radiation emitting source is a fly focal spot source.

12. A method of retrofitting energy differentiating detectors in an existing image scanner for reconstructing an image, the image scanner rotating an radiation emitting source along a first path around a predetermined center while continuously emitting energy towards an object, the image scanner rotating an energy integrating detector for detecting intensity data along a second path around the predetermined center, comprising
    fixedly placing a predetermined number of energy differentiating detectors along a third path around the predetermined center, third path being inside the first path, the energy differentiating detectors detecting spectral data;
    reconstructing an image based upon the intensity data and the spectral data; and
    providing an outer high-Z material shielding layer and an inner low-Z material shielding layer on an outer surface of each of the energy differentiating detectors, the outer surface being closer to the radiation emitting source than an inner surface of the energy differentiating detectors.

13. The method of retrofitting an existing image scanner for reconstructing an image according to claim 12 further comprising an additional step of correcting the intensity data based upon blockage of the radiation caused by the energy differentiating detectors.

14. The method of retrofitting an existing image scanner for reconstructing an image according to claim 12 further comprising an additional step of correcting the spectral data based upon blockage of the radiation caused by the energy differentiating detectors.

15. The method of retrofitting an existing image scanner for reconstructing an image according to claim 12 wherein the energy differentiating detectors include photon counting detectors.

16. The method of retrofitting an existing image scanner for reconstructing an image according to claim 12 wherein the energy differentiating detectors are sparsely placed.

17. An apparatus for reconstructing an image, comprising:
a predetermined number of energy differentiating detectors fixedly placed along a first path around an object to be scanned by a scanner;
at least one radiation emitting source moving along a predetermined second path outside the first path while said radiation emitting source continuously emitting radiation towards the object and said energy differentiating detectors detecting spectral data, the fixedly placed energy differentiating detectors being stationary on the first path with respect to the moving radiation emitting source; and
an image reconstruction unit for reconstructing an image based upon the spectral data;
an inner low-Z material shielding layer placed on at least an outer surface of each of said energy differentiating detectors, the outer surface being closer to said radiation emitting source than an inner surface of said energy differentiating detectors; and
an outer high-Z material shielding layer placed on said inner low-Z material shielding layer.

18. The apparatus for reconstructing an image according to claim 17 further comprises at least one energy integrating detector for detecting intensity data while said energy integrating detector moving along a predetermined third trajectory around the object, said image reconstruction unit reconstructing the image based upon the intensity data and the spectral data.

19. The apparatus for reconstructing an image according to claim 17 wherein said radiation emitting source modulates a combination of a radiation energy level and an intensity level over time.

20. The apparatus for reconstructing an image according to claim 18 further comprises a correction unit for correcting the intensity data based upon blockage of the radiation caused by said energy differentiating detectors.

21. The apparatus for reconstructing an image according to claim 17 further comprises a correction unit for correcting the spectral data based upon blockage of the radiation caused by said energy differentiating detectors.

22. The apparatus for reconstructing an image according to claim 20 whereas said correction unit corrects based upon view-by-view calibration.

23. The apparatus for reconstructing an image according to claim 17 wherein said energy differentiating detectors include photon counting detectors.

24. The apparatus for reconstructing an image according to claim 17 wherein said energy differentiating detectors include semiconductor direct conversion detectors.

25. The apparatus for reconstructing an image according to claim 17 wherein said energy differentiating detectors are sparsely placed within a predetermined range of less than 150 detectors.

26. The apparatus for reconstructing an image according to claim 17 further comprises a table moving unit for moving the object along a predetermined direction while the spectral data is being collected.

27. The apparatus for reconstructing an image according to claim 17 wherein at least said one radiation emitting source is a fly focal spot source.

28. A modular device for retrofitting energy differentiating detectors in an existing image scanner for reconstructing an image, the image scanner rotating an radiation emitting source along a first path around a predetermined center while continuously emitting energy towards an object, the image scanner rotating an energy integrating detector for detecting intensity data along a second path around the predetermined center, comprising
a predetermined number of energy differentiating detectors for detecting spectral data; and
a module housing for housing a predetermined number of said energy differentiating detectors fixedly placed along a third path, third path being inside the first path as said module housing is retrofitted into the existing image scanner, whereas the scanner reconstructs an image based upon the intensity data and the spectral data;
an inner low-Z material shielding layer placed on at least an outer surface of each of said energy differentiating detectors, the outer surface being closer to said radiation emitting source than an inner surface of said energy differentiating detectors; and
an outer high-Z material shielding layer placed on said inner low-Z material shielding layer.

29. The modular device for retrofitting an existing image scanner for reconstructing an image according to claim 28 further comprises a correction unit for correcting the intensity data based upon blockage of the radiation caused by said energy differentiating detectors.

30. The modular device for retrofitting an existing image scanner for reconstructing an image according to claim 28 further comprises a correction unit for correcting the spectral data based upon blockage of the radiation caused by said energy differentiating detectors.

31. The modular device for retrofitting an existing image scanner for reconstructing an image according to claim 29 whereas said correction unit corrects based upon view-by-view calibration.

32. The modular device for retrofitting an existing image scanner for reconstructing an image according to claim 28 wherein said energy differentiating detectors include photon counting detectors.

33. The modular device for retrofitting an existing image scanner for reconstructing an image according to claim 28 wherein said energy differentiating detectors include semiconductor direct conversion detectors.

34. The modular device for retrofitting an existing image scanner for reconstructing an image according to claim 28 wherein said energy differentiating detectors are sparsely placed within a predetermined range of less than 150 detectors.

* * * * *